United States Patent [19]

Wiezer

[11] Patent Number: 4,562,220

[45] Date of Patent: Dec. 31, 1985

[54] POLYALKYLDIAZASPIRODECANYLA- CETIC ACID DERIVATIVES, A PROCESS FOR THEIR PREPARATION AND THEIR USE AS LIGHT STABILIZERS FOR ORGANIC POLYMERS

[75] Inventor: Hartmut Wiezer, Lützelburg, Fed. Rep. of Germany

[73] Assignee: Hoechst Aktiengesellschaft, Fed. Rep. of Germany

[21] Appl. No.: 723,718

[22] Filed: Apr. 17, 1983

Related U.S. Application Data

[63] Continuation of Ser. No. 490,540, May 2, 1983, abandoned.

[30] Foreign Application Priority Data

May 12, 1982 [DE] Fed. Rep. of Germany ....... 3217734

[51] Int. Cl.[4] .................. C07D 498/10; C07D 498/20; C07D 211/78; C08K 5/35
[52] U.S. Cl. ...................................... 524/95; 544/222; 546/19
[58] Field of Search .......................... 524/95; 544/222; 546/19

[56] References Cited

U.S. PATENT DOCUMENTS

| | | | |
|---|---|---|---|
| 3,941,744 | 3/1976 | Murayama | 524/100 |
| 4,066,615 | 7/1978 | Murayama | 524/95 |
| 4,107,139 | 8/1978 | Mayer et al. | 524/95 |
| 4,110,334 | 8/1978 | Mayer et al. | 524/95 |
| 4,191,684 | 3/1980 | Wiezer | 524/95 |
| 4,220,773 | 9/1980 | Wiezer et al. | 546/19 |
| 4,247,449 | 1/1981 | Wiezer | 524/95 |
| 4,319,030 | 3/1982 | Wiezer et al. | 546/19 |
| 4,340,534 | 7/1982 | Wiezer et al. | 524/95 |
| 4,408,051 | 10/1983 | Hinsken et al. | 546/19 |
| 4,419,512 | 12/1983 | Karrer | 546/19 |
| 4,526,966 | 7/1985 | Wiezer | 546/19 |

FOREIGN PATENT DOCUMENTS

| | | |
|---|---|---|
| 1207 | 4/1979 | European Pat. Off. . |
| 8084 | 2/1980 | European Pat. Off. . |
| 22997 | 1/1981 | European Pat. Off. . |
| 25867 | 4/1981 | European Pat. Off. . |
| 2227689 | 12/1972 | Fed. Rep. of Germany . |
| 2933732 | 3/1981 | Fed. Rep. of Germany . |
| 2089800 | 6/1982 | United Kingdom . |

OTHER PUBLICATIONS

Lloyd N. Ferguson-Textbook of Organic Chemistry, 260-263 (1961).
Carl R. Noller-Textbook of Organic Chemistry, 178, 179, 184 and 185 (1958).

*Primary Examiner*—Veronica P. Hoke
*Attorney, Agent, or Firm*—Connolly and Hutz

[57] ABSTRACT

New polyalkyldiazaspirodecanylacetic acid derivatives are prepared by reacting diazaspirodecanes of the formula

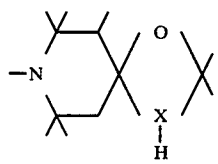

in which X is

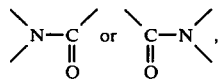

with halogenoacetic acid derivatives, and, if desired, reacting products thus obtained further with alcohols or amines. The compounds can be used as light stabilizers for plastics and lacquers.

11 Claims, No Drawings

POLYALKYLDIAZASPIRODECANYLACETIC ACID DERIVATIVES, A PROCESS FOR THEIR PREPARATION AND THEIR USE AS LIGHT STABILIZERS FOR ORGANIC POLYMERS

This application is a continuation of application Ser. No. 490,540 filed May 2, 1983, which is now abandoned.

Numerous unsubstituted and substituted diazaspirodecanes of the oxazolidinone type are known from the literature. Thus, German Pat. Nos. 2,606,026 and 2,634,957 describe compounds belonging to this class which are not substituted on the oxazolidinone nitrogen and which are distinguished by a quite good stabilizing effectiveness, but they also suffer, in some cases, from considerable disadvantages, especially in respect of volatility and also inadequate solubility in some plastics. The result of this is that these products cannot be employed universally, i.e. not with equal success in several fields, such as, for example, the paint sector and the plastics sector.

There has, therefore, been no lack of attempts to eliminate these disadvantages by enlarging the molecule or by means of substitution on the polar NH group by alkyl radicals. Thus, European Pat. No. 17,617 describes diazaspirodecanes which are substituted on the oxazolidinone nitrogen, but which are not technically satisfactory, particularly because of their excessive volatility. As opposed to this, the N-alkyldiazaspirodecanes which are known from German Offenlegungsschrift No. 2,933,732 possess in some cases a remarkably low volatility, but can only be prepared with difficulty and in an unsatisfactory yield.

The present invention is, therefore, based on the object of synthesizing diazaspirodecane derivatives which have a good action and a low volatility and are thoroughly compatible with the polymers to be stabilized, importance being attached to high yields, as a further criterion.

It has been found that diazaspirodecanylacetic acid derivatives which are accessible relatively easily and in good yields surprisingly fulfill these requirements to a considerable extent.

The new compounds correspond to the general formula (I)

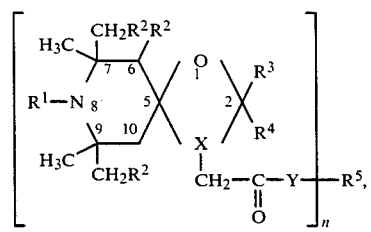

in which X denotes a group of the formula (II) or (III)

(II)

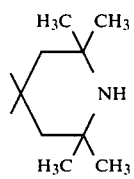

(III)

in which the indices 3 and 4 indicate the ring position in the diazaspirodecane system, and the free valency of the nitrogen atom 3 or 4 effects the linkage with the acetic acid radical.

$R^1$ is hydrogen, oxygen or $C_1$ to $C_{12}$ alkyl, preferably hydrogen, oxygen or $C_1$ to $C_4$ alkyl and especially hydrogen, and $R^2$ is hydrogen or a $C_1$ to $C_5$ alkyl group, preferably hydrogen or a methyl group and, particularly, hydrogen.

$R^3$ represents hydrogen, $C_1$ to $C_{30}$, preferably $C_1$ to $C_{18}$ and, particularly, $C_1$ to $C_5$, alkyl, a phenyl or naphthyl group which can be monosubstituted or disubstituted by chlorine or $C_1$ to $C_4$ alkyl, preferably phenyl, or a $C_7$ to $C_{12}$ phenylalkyl group which can be substituted by a $C_1$ to $C_4$ alkyl radical, preferably a benzyl group.

$R^4$ denotes hydrogen, $C_1$ to $C_{30}$, preferably $C_1$ to $C_{18}$, and especially $C_1$ to $C_{13}$, alkyl, phenyl or naphthyl which can be monosubstituted or disubstituted by chlorine or $C_1$ to $C_4$ alkyl, preferably phenyl, or $C_7$ to $C_{12}$ phenylalkyl which can be substituted by a $C_1$ to $C_4$ alkyl radical, but preferably denotes benzyl.

$R^3$ and $R^4$, together with the carbon atom linking them, can also represent a $C_5$ to $C_{18}$, preferably $C_5$ to $C_{12}$, cycloalkyl group which can be substituted by up to four $C_1$ to $C_4$ alkyl groups, preferably methyl groups, or can represent a group of the formula

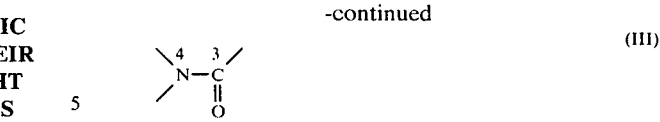

n denotes an integer from 1 to 6, preferably 1 to 4 and especially 1 to 3.

If n=1, $R^5$ denotes hydrogen, $C_1$ to $C_{18}$, preferably $C_1$ to $C_{12}$, alkyl, $C_7$ to $C_9$ phenylalkyl which can be monosubstituted or disubstituted by $C_1$ to $C_4$ alkyl, or $C_3$ to $C_{12}$ alkenyl, or represents a 2,2,6,6-tetramethyl-4-piperidinyl group.

If n=2, $R^5$ is a $C_2$ to $C_{30}$, preferably $C_2$ to $C_{18}$ and especially $C_2$ to $C_6$, alkylene group or a $C_4$ to $C_8$ alkenylene group or a $C_2$ to $C_{12}$ bis-(propoxy)-alkylene group or a monocycloalkylene, dicycloalkylene or tricycloalkylene which has 6 to 18, preferably 6 to 12, carbon atoms and which can be substituted by up to four methyl groups, but is preferably not substituted, it being possible, in the case first mentioned, for two carbon atoms to be replaced by nitrogen atoms which can carry propylene groups, or $R^5$ is $C_6$ to $C_{18}$ arylene, preferably phenylene, or $C_7$ to $C_{18}$ aralkylene.

If n=3, $R^5$ is a $C_3$ to $C_6$ alkanetriyl radical or a radical of the formula

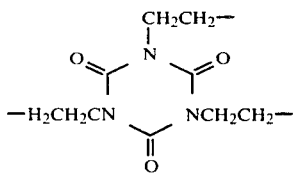

or a di-$C_2$-alkylenetriamine to di-$C_4$-alkylenetriamine radical.

If n=4 to 6, $R^5$ is a $C_4$ to $C_{10}$ alkan-n-yl radical which can contain an ether group, or is a tri-($C_2$ to $C_4$) to penta-($C_2$ to $C_4$) radical, preferably a tri-$C_2$-alkylenetetra-bis-hexamine to penta-$C_2$-alkylenetetra-bis-hexamine radical.

Y represents —O— or

in which $R^6$ has one of the meanings indicated under $R^5$ in the case where n=1.

The following are examples of polyalkyldiazaspirodecanylacetic acid derivatives according to the invention:

1. Ethyl 2,2,7,7,9,9-hexamethyl-1-oxa-3,8-diaza-4-oxospiro-[4,5]-decan-3-ylacetate
2. Ethyl 2,2,7,7,9,9-hexamethyl-1-oxa-4,8-diaza-3-oxospiro-[4,5]-decan-4-ylacetate
3. 2,2,6,6-Tetramethyl-4-piperidinyl-2,2,7,7,9,9-hexamethyl-1-oxa-3,8-diaza-4-oxospiro-[4,5]-decan-3-ylacetate
4. Ethanebis-(2,2,7,7,9,9-hexamethyl-1-oxa-4,8-diaza-3-oxospiro-[4,5]-decan-4-yl)-acetamide
5. Ethyl 7,7,9,9-tetramethyl-2,2-diethyl-1-oxa-3,8-diaza-4-oxospiro-[4,5]-decan-3-ylacetate
6. 1,4-Butanebis-(7,7,9,9-tetramethl-2,2-diethyl-1-oxa-3,8-diaza-4-oxospiro-[4,5]-decan-3-yl)-acetate
7. 1,6-Hexanebis-(7,7,9,9-tetramethyl-2,2-diethyl-1-oxa-3,8-diaza-4-oxospiro-[4,5]-decan-3-yl)-acetate
8. 1,6-Hexanebis-(7,7,9,9-tetramethyl-2,2-diethyl-1-oxa-3,8-diaza-4-oxospiro-[4,5]-decan-3-yl)-acetamide
9. 2,2,6,6-Tetramethyl-4-piperidinyl-7,7,9,9-tetramethyl-2,2-diethyl-1-oxa-3,8-diaza-4-oxospiro-[4,5]-decan-3-ylacetate
10. Methyl 7,7,9,9-tetramethyl-2-ethyl-2-pentyl-1-oxa-3,8-diaza-4-oxospiro-[4,5]-decan-3-ylacetate
11. Methyl 2,7,7,9,9-pentamethyl-2-propyl-1-oxa-3,8-diaza-4-oxospiro-[4,5]-decan-3-ylacetate
12. Methyl 2,2,7,7,9,9-pentamethyl-2-undecyl-1-oxa-3,8-diaza-4-oxospiro-[4,5]-decan-3-ylacetate
13. Methyl 2,2,4,4-tetramethyl-10-tert.-butyl-7-oxa-3,13-diaza-14-oxodispiro-[5.1.4.2]-tetradecan-13-ylacetate
14. 2,7,7,9,9-Pentamethyl-2-undecyl-1-oxo-3,8-diaza-4-oxospiro-[4,5]-decan-3-ylacetamide
15. Glycol bis-(2,2,4,4-tetramethyl-10-tert.-butyl-7-oxa-3,13-diaza-14-oxodispiro-[5.1.4.2]-tetradecan-13-yl)acetate
16. Glycol bis-(2,7,7,9,9-pentamethyl-2-benzyl-1-oxa-3,8-diaza-4-oxospiro-[4,5]-decan-3-yl)-acetate
17. 7,7,9,9-Tetramethyl-2,2,-dibenzyl-1-oxa-3,8-diaza-4-oxospiro-[4,5]-decan-3-yl)-acetamide
18. 2,7,7,9,9-Pentamethyl-2-benzyl-1-oxa-3,8-diaza-4-oxospiro-[4,5]-decan-3-yl)-acetamide
19. Ethyl 7,7,9,9-tetramethyl-2,2-dibenzyl-1-oxa-3,8-diaza-4-oxospiro-[4,5]-decan-3-ylacetate
20. Ethyl 2,2,4,4-tetramethyl-7-oxa-3,20-diaza-21-oxodispiro-[5.1.11.2]-heneicosan-20-ylacetate
21. 2,2,6,6-Tetramethyl-4-piperidinyl-2,2,4,4-tetramethyl-7-oxa-3,20-diaza-21-oxodispiro-[5.1.11.2]-heneicosan-20-ylacetate
22. Hexyl 2,2,4,4-tetramethyl-7-oxa-3,20-diaza-21-oxodispiro-[5.1.11.2]-heneicosan-20-ylacetate
23. 2-Ethylhexyl 2,2,4,4-tetramethyl-7-oxa-3,20-diaza-21-oxodispiro-[5.1.11.2]-heneicosan-20-ylacetate
24. Propanetriyl tris-(2,2,4,4-tetramethyl-7-oxa-3,20-diaza-21-oxodispiro-[5.1.11.2]-heneicosan-20-yl)-acetate
25. Hexanediyl bis-(2,2,4,4-tetramethyl-7-oxa-3,20-diaza-21-oxodispiro-[5.1.11.2]-heneicosan-20-yl)-acetate
26. 1,6-Hexanebis-(2,2,4,4-tetramethyl-7-oxa-3,20-diaza-21-oxodispiro-[5.1.11.2]-heneicosan-20-ylacetamide
27. N,N′-3(4),8(9)-Bismethylenetricyclo-[5.2.1.0$^{2,6}$]-decanebis-(2,2,4,4-tetramethyl-7-oxa-3,20-diaza-21-oxidispiro-[5.1.11.2]-heneicosan-20-yl)-acetamide
28. Propanetriyl tris-(2,2,7,7,9,9-hexamethyl-1-oxa-4,8-diaza-3-oxospiro-[4,5]-decan-4-yl)-acetate
29. Tris-(1,3,5-triethylenetriazine-2,4,6-trione) 2,2,7,7,9,9-hexamethyl-1-oxa-3,8-diaza-4-oxospiro-[4,5]-decan-3-ylacetate
30. N,N′-(3(4),8(9)-Bismethylenetricyclo-[5.2.1.0$^{2,6}$]-decanebis-(2,2,7,7,9,9-hexamethyl-1-oxa-3,8-diaza-4-oxospiro-[4,5]-decan-3-yl)-acetamide
31. Ethyl 2,2,4,4-tetramethyl-7-oxa-3,13-diaza-14-oxodispiro-[5.1.4.2]-tetradecan-3-ylacetate The new diazaspirodecanylacetic acid derivatives are prepared in accordance with the diagram outlined below from the compounds of German Pat. Nos. 2,606,026, 2,634,957 and 2,834,962 (IV) by reacting the latter with halogenoacetic acid derivatives (V), either in a single process stage in accordance with route A or, in accordance with route B, from methyl or ethyl esters (Ia) which have been obtained in accordance with route A, by transesterifying the latter with alcoholic compounds or amidating them with compounds (VI) carrying amino groups.

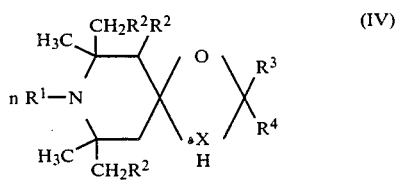

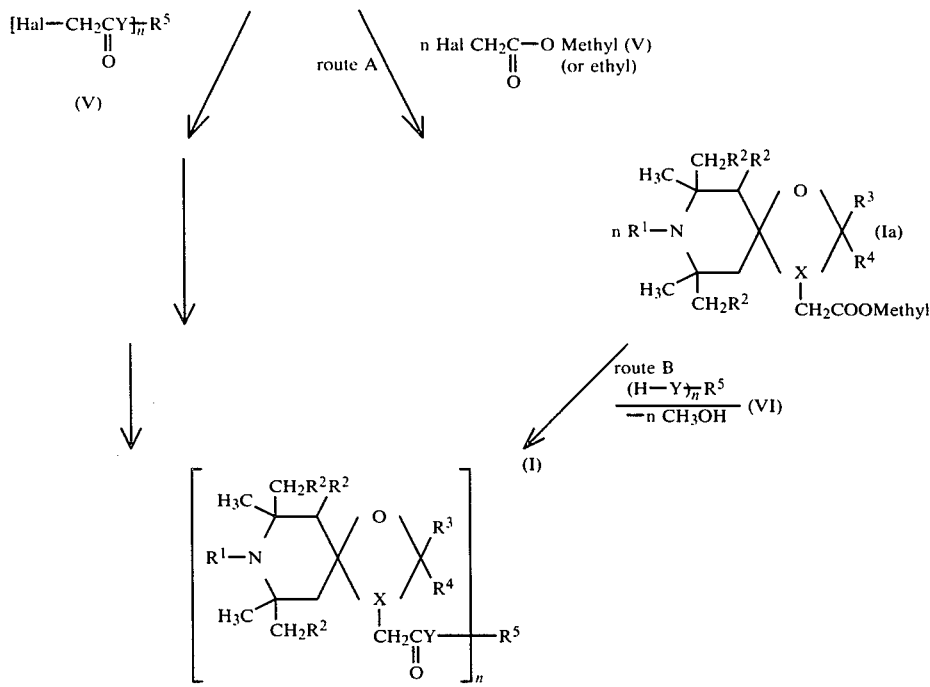

In the formulae of the diagram of reactions, $R^1$, $R^2$, $R^3$, $R^4$, $R^5$, n, X and Y have the meanings indicated above; Hal is chlorine or bromine.

The detailed procedure followed in the preparation is first to prepare the corresponding salts from the diazaspirodecanes of the formula (IV) by reacting the latter with alkali metal hydrides, alcoholates or hydroxides, and then to react these salts in accordance with route A at temperatures of 100 to 200, preferably 120 to 200 and especially 140° to 200, °C., in inert organic solvents, such as, for example, toluene, xylene or dimethylformamide, at ordinary pressure or under pressure, with halogenoacetic acid derivatives (V) to give the desired compounds of the formula (I). It is also possible, and advantageous in many cases, to convert the methyl or ethyl esters (Ia), which can be obtained in accordance with route A and which constitute a part of the invention, into other products according to the invention in accordance with route B by transesterification or amidation. The latter reactions are carried out at the reaction temperatures mentioned above, preferably in aromatic hydrocarbons as solvents, with the addition of customary catalysts, such as, for example, $LiNH_2$, $NaOCH_3$, $Ti(O-i-prop)_4$ and the like.

It was surprising and could not have been foreseen that the polyalkyldiazaspirodecanylacetic acids according to the invention would be markedly less volatile than the corresponding alkyl derivatives of European Pat. No. 17,617 or of German Offenlegungsschrift No. 2,933,732. It would rather have been expected that, owing to the similar molecular structure, volatilities of a similar level would also have been observed at approximately equal molecular weights. Furthermore, it could in no way have been foreseen that the ester derivatives, in particular, would be more suitable for stabilizing lacquers than the alkyl products quoted, because of their similar polarity. All in all, therefore, technical advantages in use would not have been expected compared with the compounds of the state of the art which have been quoted. The total pattern of technical properties in use, which stands out in comparison with these compounds, must, therefore, be regarded as extremely surprising.

The low volatility of the new products in which n=1 must also be especially surprising to those skilled in the art. It is certainly known from German Offenlegungsschrift No. 2,933,732 that alkylated monodiazaspirodecanes have quite a high volatility.

As already stated, the new compounds are used as stabilizes for plastics to protect the latter against damage caused by the action of oxygen, heat and light. Examples of such plastics and of additives which can also be employed additionally are mentioned on pages 14 to 19 of German Offenlegungsschrift No. 3,045,839.

The products according to the invention are particularly suitable for stabilizing homopolymers and copolymers of ethylene, propylene, butadiene, (meth)acrylic acid derivatives, particularly esters thereof, and styrene, in which cases they are generally employed in amounts of 0.01 to 5, preferably 0.05 to 2.5 and particularly 0.1 to 1.0, % by weight, relative to the material to be stabilized—if appropriate together with other substances having a stabilizing action. The products in which Y is —O— are particularly suitable for stabilizing lacquer systems.

The examples which follow serve to illustrate the subject of the invention in greater detail.

In the following preparation examples, the process products are characterized by numbers which relate to the numbering of the compounds listed on pages 6, 7 and 8.

EXAMPLE 1

(compound No. 20)

109.2 g (0.3 mole) of dry 2,2,4,4-tetramethyl-7-oxa-3,20-diaza-21-oxodispiro-[4,5]-heneicosane are initially taken in 400 ml of anhydrous xylene. 9.0 g (0.3 mole) of 80% strength NaH/paraffin mixture are added and the mixture is heated to reflux temperature in the course of one hour, after which it is stirred until the evolution of hydrogen is complete (a further 3 hours). The mixture is then cooled to 20° C. and a solution of 50 ml of anhydrous xylene and 51.0 g (0.3 mole) of ethyl bromoacetate is added dropwise. The mixture is then stirred under reflux for 8 hours, then filtered while hot (38 g of NaBr), the filtrate is concentrated to dryness in vacuo and the residue is recrystallized from n-heptane.

Yield: 119.8 g=88% of theory; melting point 154° C.

EXAMPLES 2 TO 18

The procedure employed is analogous to Example 1, using the spirodecane which can be derived in each case from the list of process products on pages 6, 7 and 8, and the halogenoacetic acid derivative specified in the table below.

| Example No. | Halogenoacetic acid derivative employed | Process product Compound No. | m.p. (°C.) |
|---|---|---|---|
| 2 | BrCH$_2$COOC$_2$H$_5$ | 19 | 149 |
| 3 | " | 30 | 91 |
| 4 | " | 5 | 74–6 |
| 5 | " | 1 | 83 |
| 6 | " | 2 | 111 |
| 7 | ClCH$_2$COOCH$_3$ | 10 | 68 |
| 8 | " | 11 | 86 |
| 9 | " | 12 | 73 |
| 10 | " | 13 | 114 |
| 11 | ClCH$_2$CONH$_2$ | 14 | 85 |
| 12 | " | 17 | 233 |
| 13 | " | 18 | 160 |
| 14 | ClCH$_2$COO—[2,2,6,6-tetramethylpiperidine] | 3 | 99 |
| 15 | " | 9 | 92 |
| 16 | " | 21 | 135 |
| 17 | (ClCH$_2$COOCH$_2$)$_2$ | 15 | 154 |
| 18 | " | 16 | 172 |

EXAMPLE 19

(compound No. 7)

27.5 g (0.077 mole) of compound No. 5 prepared in accordance with Example 4, 4.6 g (0.039 mole) of 1,6-hexanediol and 0.5 g of LiNH$_2$ in 150 g of anhydrous mesitylene are stirred under reflux for 15 hours, in the course of which 3.5 g of ethanol are removed by distillation through a 10 cm Vigreaux column. The mixture is then filtered while hot and the filtrate is concentrated to dryness in vacuo. The oily product which remains is crystallized from hexane.

Yield: 25.5 g=89% of theory; melting point 154° C.
MW: 715 (theory 734)

EXAMPLES 20 TO 31

The procedure is analogous to that of Example 19

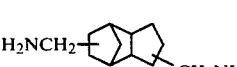

| Example No. | Alcohol or amine | Educt (Ia) = compound No. | Process product Compound No. | m.p. (°C.) |
|---|---|---|---|---|
| 20 | 2-Ethylhexanol | 20 | 22 | oil |
| 21 | n-Hexan-1-ol | 20 | 23 | oil |
| 22 | Glycerol | 20 | 24 | resin |
| 23 | 1,6-Hexamethylenediamine | 5 | 8 | 187 |
| 24 | 1,6-Hexanediol | 20 | 25 | 68 |
| 25 | H$_2$NCH$_2$—[bicyclic]—CH$_2$NH$_2$ | 1 | 30 | 105 |
| 26 | HOCH$_2$CH$_2$N(C=O)N(CH$_2$CH$_2$OH)(C=O)N—CH$_2$CH$_2$OH | 1 | 29 | 90 |
| 27 | Glycerol | 2 | 28 | 86 |
| 28 | as in Example 25 | 20 | 27 | 100 |
| 29 | Ethylenediamine | 2 | 4 | 248 |
| 30 | 1,6-Hexamethylenediamine | 20 | 26 | 178 |
| 31 | 1,6-Hexanediol | 5 | 7 | 77 |

EXAMPLE 32

This example demonstrates the volatility of the stabilizers according to the invention, compared with products of the state of the art.

The volatility figures were determined in an apparatus for thermogravimetric analysis. Equal quantities (500 mg) of the stabilizers according to the invention and of the comparison substances were heated to 300° C. in an atmosphere of nitrogen at a rate of heating of 2 K/minute, and the loss of substance, in mg/cm$^2$ of sample surface, was measured. The results are shown in the table below:

| Stabilizer according to Example | Loss of weight in mg/cm$^2$ on reaching °C. | | | |
|---|---|---|---|---|
| | 220 | 260 | 300 | 10 minutes at 300 |
| 30 | 0.16 | 0.63 | 1.90 | 3.16 |
| 1 | 0.95 | 4.74 | 19.28 | 32.70 |
| 23 | 0.47 | 0.79 | 3.48 | 5.37 |
| Comparison[1] | 0.01 | 0.23 | 2.05 | 3.79 |
| Comparison[2] | 0.79 | 3.63 | 13.27 | 20.22 |
| Comparison[3] | 2.73 | 6.36 | 30.02 | 52.14 |

[1] Compound according to Example 70 of German Auslegeschrift 2,933,732
[2] Compound according to Example 4 of German Auslegeschrift 2,933,732
[3] Compound according to Example 63 of German Auslegeschrift 2,933,732

EXAMPLE 33

A mixture, prepared in a laboratory high-speed mixer, of:

100 parts by weight of polypropylene (®Hostalen PPU VP 1770 F made by Hoechst AG having a melt index MFI 190/5 of 1.9 g/10 minutes, determined as specified in DIN 53,535), 0.2 part by weight of calcium stearate, 0.1 part by weight of pentaerythrityl tetrakis-3-(3,5-di-tert.-butyl-4-hydroxyphenyl)-propionate and 0.3 part by weight of the stabilizer to be tested, is converted into granules. The material stabilized in this way is then melted in a laboratory extruder under the customary processing conditions and is spun into monofilaments via a spinning pump having an eight-orifice spinning nozzle. These monofilaments are then subsequently stretched in a 1:3 ratio and are texturized to form yarn of 40 detex, which is converted into test fabrics.

The fabric samples are mounted on a perforated piece of cardboard so that a free aperture of approx. 15.5 mm diameter is left and are subjected in this form to irradiation with alternating light in a Xenotest X-1200 apparatus made by Original Hanau Quartzlampen GmbH. The intensity of the radiation is modulated by a UV filter (special filter glass, d=1.7 mm), and the test method specified in DIN 53,387 (17 minutes dry period, 3 minutes sprinkling, black panel temperature 45° C., relative atmospheric humidity during the drying period 70 to 75%) is used. At specific intervals of time the fabrics are loaded centrally using a weight of diameter 6 mm and a pressure of $0.1N/mm^2$. The time when the weight breaks through is taken as the time of breakdown.

| Stabilizer according to Example No. | Exposure time in hours |
|---|---|
| 23 | 900$^{(x)}$ |
| 24 | 900$^{(x)}$ |
| Comparison$^{(1)}$ | 900 |
| Comparison$^{(2)}$ | 800 |

$^{(1)}$Compound according to Example 70 of German Auslegeschrift 2,933,732
$^{(2)}$Compound according to Example 4 of German Auslegeschrift 2,933,732
$^{(x)}$Weight not yet broken through

I claim:
1. A polyalkyldiazaspirodecanylacetic acid derivative of the general formula (I)

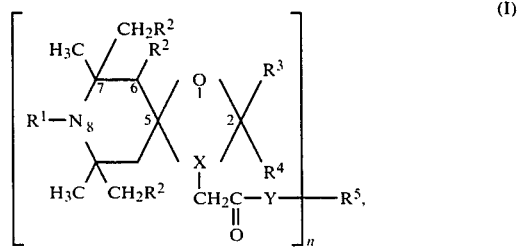
(I)

in which X denotes a group of the formula (II) or (III)

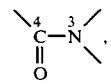
(II)

(III)

in which the indices 3 and 4 indicate the ring position in the diazaspirodecane system, and the free valency of the nitrogen atom 3 or 4 effects the linkage with the acetic acid radical, $R^1$ is H, O or $C_1$ to $C_{12}$ alkyl, $R^2$ is H or a $C_1$ to $C_5$ alkyl group, $R^3$ and $R^4$ are identical or different and represent H, a $C_1$ to $C_{30}$ alkyl group, a phenyl or naphthyl group which can be substituted by chlorine or $C_1$ to $C_4$ alkyl, or a $C_7$ to $C_{12}$ phenylalkyl group which can be substituted by $C_1$ to $C_4$ alkyl, or $R^3$ and $R^4$, together with the carbon atom linking them, also denote a $C_5$ to $C_{18}$ cycloalkyl group which can be substituted by up to four $C_1$ to $C_4$ alkyl groups, or a group of the formula

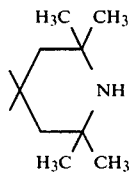

n represents an integer from 1 to 6 and, if n=1, $R^5$ denotes H, $C_1$ to $C_{18}$ alkyl, $C_3$ to $C_{12}$ alkenyl, $C_7$ to $C_9$ phenylalkyl which can be substituted by $C_1$ to $C_4$ alkyl, or a 2,2,6,6-tetramethyl-4-piperidinyl group, if n=2, $R^5$ is $C_2$ to $C_{30}$ alkylene, a $C_4$ to $C_8$ alkenylene group, a $C_2$ to $C_{12}$ bis-(propyleneoxy)-alkylene group or a monocycloalkylene, dicycloalkylene or tricycloalkylene which has 6 to 18 carbon atoms and which can be substituted by up to four methyl groups, it being possible, in the case first mentioned, for two carbon atoms to be replaced by nitrogen atoms which can carry propylene groups, or $R^5$ is $C_6$ to $C_{18}$ arylene or $C_7$ to $C_{18}$ aralkylene, if n=3, $R^5$ denotes $C_3$ to $C_6$ alkanetriyl or a radical of the formula

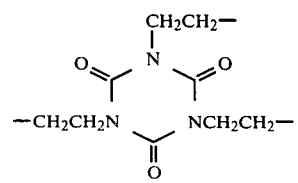

or a di-$C_2$-alkylenetriamino to di-$C_4$-alkylenetriamino radical and, if n=4 to 6, $R^5$ represents a $C_4$ to $C_{10}$ alkan-n-yl radical which can contain an ether group, or represents a tri-$C_2$ to $C_4$ alkylenetetra-bis-hexamino to penta-$C_2$ to $C_4$-alkylenetetra-bis-hexamino radical, and Y is —O— or

in which $R^6$ has one of the meanings indicated under $R^5$ in the case where n=1.

2. A process for the preparation of a compound as claimed in claim 1, which comprises converting an azaspirodecane of the formula (IV)

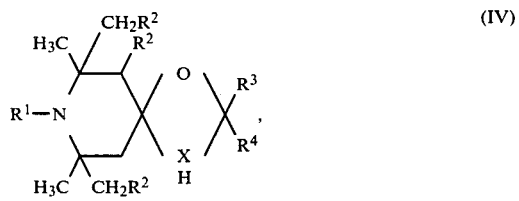
(IV)

into an alkali metal salt thereof by reacting it with an equivalent quantity of an alkali metal hydride, alcoholate or hydroxide in an inert organic solvent at 50° to 160° C., and then reacting this salt, at 100° to 200° C. in an inert organic solvent, with an equivalent quantity of a halogen compound of the formula (V)

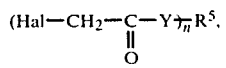   (V)

in which Hal=Cl or Br.

3. The process as claimed in claim 2, wherein the alkali metal salt of the compound (IV) is first reacted with a methyl or ethyl halogenoacetate, whereby a compound of the formula (I) in which $n=1$, $Y=-O-$ and $R^5=CH_3$ or $C_2H_5$ is obtained, and this compound is then reacted, in an inert organic solvent at 100° to 200° C., in the presence of alkaline catalysts, with an equivalent quantity of a compound of the formula (VI)

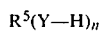   (VI)

4. A compound as claimed in claim 1 in which Y is —O—.

5. A compound as claimed in claim 1, wherein X denotes a group of said formula III.

6. A compound as claimed in claim 1, wherein Y is —N(R_6)—.

7. A compound as claimed in claim 1, wherein X denotes a group of said formula III, and Y is —N(R_6)—.

8. A synthetic polymer which has been stabilized against decomposition by ultraviolet light and which contains 0.01 to 5 parts by weight, relative to the polymer, of a compound as claimed in claim 1.

9. An ultraviolet-stabilized synthetic polymer according to claim 8, said polymer being a homopolymer or copolymer of ethylene, propylene, butadiene, acrylic acid or derivatives thereof, methacrylic acid or derivatives thereof, or styrene.

10. An ultraviolet-stabilized polymer according to claim 9 which contains 0.05 to 2.5 percent by weight of the stabilizer compound wherein Y is —O—.

11. A process for stabilizing synthetic polymers against the harmful effect of ultraviolet light, which comprises adding to the polymer 0.01 to 5 parts by weight, relative to the polymer, of a stabilizer as claimed in claim 1.

* * * * *